(12) United States Patent
Rousche et al.

(10) Patent No.: US 10,213,548 B2
(45) Date of Patent: Feb. 26, 2019

(54) SYSTEMS AND METHODS FOR AUTOMATIC TERMINATION OF FLOW DUE TO NEEDLE DISLODGEMENT

(71) Applicant: Hemotek Medical Incorporated, Rohnert Park, CA (US)

(72) Inventors: Patrick Rousche, Healdsburg, CA (US); Peter Tek, Orland Park, IL (US); Charles Ventura, Cary, IL (US); Richard A. Scribner, Shingle Springs, CA (US)

(73) Assignee: Hemotek Medical Incorporated, Rohnert Park, CA (US)

( * ) Notice: Subject to any disclaimer, the term of this patent is extended or adjusted under 35 U.S.C. 154(b) by 174 days.

(21) Appl. No.: 15/286,274

(22) Filed: Oct. 5, 2016

(65) Prior Publication Data

US 2017/0021098 A1    Jan. 26, 2017

Related U.S. Application Data

(63) Continuation-in-part of application No. PCT/US2014/072573, filed on Dec. 29, 2014.
(Continued)

(51) Int. Cl.
*A61M 5/168* (2006.01)
*A61M 5/158* (2006.01)
*A61M 39/28* (2006.01)

(52) U.S. Cl.
CPC ........ *A61M 5/16813* (2013.01); *A61M 5/158* (2013.01); *A61M 39/281* (2013.01);
(Continued)

(58) Field of Classification Search
CPC ............ A61M 5/16813; A61M 39/281; A61M 5/158; A61M 2205/276; A61M 2005/1586; A61M 2005/1588
See application file for complete search history.

(56) References Cited

U.S. PATENT DOCUMENTS 4,407,434 A   10/1983  Kempf
4,551,128 A   11/1985  Hakim et al.
(Continued)

FOREIGN PATENT DOCUMENTS

CN    101730555 A    6/2010
JP    2006-000646    1/2006
(Continued)

*Primary Examiner* — Amber Stiles
(74) *Attorney, Agent, or Firm* — Levine Bagade Han LLP

(57) ABSTRACT

Systems and methods for automatic flow termination for fluid delivery, including a housing configured for coupling a fluid delivery tube to a needle configured for subcutaneous delivery of fluid within a tissue of a patient and a spring-loaded activation mechanism having a first orientation corresponding to a condition where the housing is disposed substantially adjacent to the tissue and the needle lodged within the tissue and a second orientation corresponding to a condition where the housing is disposed away from the tissue or the needle being dislodged from the tissue. A flow termination mechanism is coupled to the activation mechanism and having an open configuration allowing flow from the fluid delivery tube to the needle when the activation mechanism is in the first orientation and a closed configuration substantially terminating flow from the fluid delivery tube to the needle when the activation mechanism is in the second orientation.

20 Claims, 9 Drawing Sheets

Related U.S. Application Data

(60) Provisional application No. 61/978,671, filed on Apr. 11, 2014.

(52) U.S. Cl.
CPC ............... *A61M 2005/1586* (2013.01); *A61M 2005/1588* (2013.01); *A61M 2205/276* (2013.01)

(56) References Cited

U.S. PATENT DOCUMENTS

| | | | |
|---|---|---|---|
| 5,300,043 A | | 4/1994 | Devlin et al. |
| 5,522,806 A | | 6/1996 | Schonbachler et al. |
| 7,044,936 B2 | | 5/2006 | Harding et al. |
| 2008/0281276 A1* | | 11/2008 | Shekalim .......... A61M 5/14244 604/250 |

FOREIGN PATENT DOCUMENTS

| | | |
|---|---|---|
| JP | 2010-526578 | 8/2010 |
| WO | WO 1993/024173 | 12/1993 |
| WO | WO 1995/015779 | 6/1995 |
| WO | WO 2008/139464 | 6/2008 |
| WO | WO 2015/156850 | 10/2015 |

* cited by examiner

SYSTEMS AND METHODS FOR AUTOMATIC TERMINATION OF FLOW DUE TO NEEDLE DISLODGEMENT

CROSS-REFERENCE TO RELATED APPLICATIONS

This application is a continuation-in-part of International Application No. PCT/US2014/072573, filed Dec. 29, 2014, which claims priority to, and the benefit of, U.S. provisional patent application Ser. No. 61/978,671 filed on Apr. 11, 2014, both of which are incorporated herein by reference in their entireties.

BACKGROUND

1. Technical Field

This disclosure pertains generally to vascular connections, and more particularly to detection and interruption of dislodged vascular connections.

2. Background Discussion

There are a number of techniques that provide a means by which to detect an errant flow of fluid through a vascular connection leading fluid from the outside of the body to the inside of the body. Common to many of these is the use of a 'continuity sensor' that looks for an interruption of energy-based signal or some mechanical connection from the tubing to the body. Such systems often use mechanical connectors, a small electrical current, a capacitance, a magnet or even ultrasound as a means of monitoring the fidelity of the connection between the body and the fluid passing element. Others use techniques designed to look for 'wetness' on the theory that a dislodged needle will leak fluid and fluid detection can be used as a surrogate marker for needle dislodgement.

BRIEF SUMMARY

An aspect of the present disclosure is a needle safety system or add-on to existing needles/tubing that uses a contact sensing mechanism on the patient's skin to determine when a given needle/tubing set that has been inserted into a patient has potentially become dislodged from that patient. This can occur when the tape holding a vascular access needle in place fails or the line is pulled out etc.

The system of the present disclosure offers important protection through the use of a fluid stop valve within the device that automatically deploys to stop the flow of fluid through a needle/tube when and only when, the needle delivering that fluid into the body is accidentally dislodged from the patient during fluid delivery. In hemodialysis that fluid is blood. In other cases, that fluid may be saline or medications. Vascular access is routinely performed in hospitals, clinics and other medical locations as well as the home (during home hemodialysis for example).

Another aspect is a device with a pinch valve configured in such a way that the valve is only activated by a mechanical linkage to a mechanical 'skinsensing' element in a needle system that has been pre-manufactured to include a compressible segment of tubing.

Another aspect is a system for sensing skin contact using a buttonlike sensor that comes straight out of the bottom of a needle body and halting flow using a blockage technique that involves rotating or sliding an opening from close to open within the needle valve.

The device of the current disclosure uses no external power, thus requires no batteries or cables, improving its ability to be adopted in medical workspaces that are complex and require simplified solutions. The device of the current disclosure is completely sterilizable and can be completely disposable. It can be manufactured relatively inexpensively using high-volume injection molding processes. It does not require extensive clinical training.

Further aspects of the technology will be brought out in the following portions of the specification, wherein the detailed description is for the purpose of fully disclosing embodiments of the technology without placing limitations thereon

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Figure 1A:
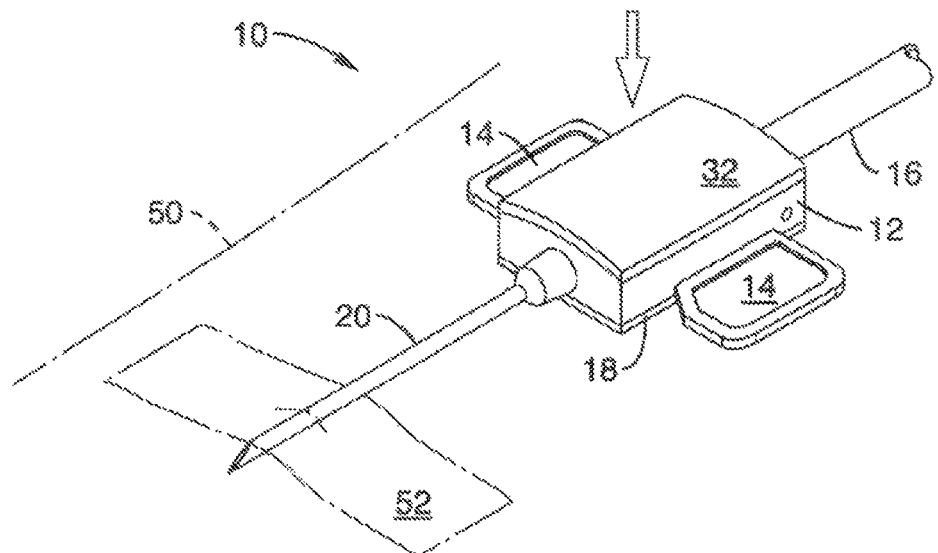
FIG. 1A is a perspective view of a sensing mechanism employing a spring arm and pinching mechanism in accordance with the present disclosure.

The sensing systems/mechanisms of the present disclosure are configured to detect separation of a vascular access needle or the associated fluid delivery tubing from the patient's skin, and act to terminate or restrict flow of the delivery fluid to the needle upon a detection or sensing of a needle separation/dislodgement.

For purposes of this disclosure, the term "sensing," particularly with respect to sensing needle dislodgement, shall be defined as a mechanical response or reaction to a needle, or device of the present disclosure in association with a needle, being dislodged or separated from the tissue of a patient.

In normal and successful vascular access, the needle delivering fluid into the body is taped to rest flat on the skin surface just behind the access point. Generally, any needle or associated tubing that is not making immediate flat contact with the skin is in danger of being dislodged.

Because the dislodged needle is not in the body, this fluid may not be reaching its intended destination. If this fluid is blood, this is a highly dangerous condition and should be treated immediately by stopping the fluid flow and re-inserting or replacing the needle.

The systems of the present disclosure use a skin contact sensor to detect when a vascular access needle is no longer in contact with the skin. In some embodiments, activation of the contact sensor also causes a secondary motion that delivers a compression lever directly onto the soft section of tubing within the flow path in the needle body for automatic restriction/reduction of the fluid flow. With the sensing mechanisms of the present disclosure, the device or add-on device can both detect and immediately stop errant fluid flow due to dislodged access needles.

FIG. 1A through FIG. 4 show an embodiment of a sensing mechanism/system 10 employing a spring arm and pinching mechanism in accordance with the present disclosure. Standard needle sets may incorporate sensing mechanism 10 to provide vascular access for blood or saline/medication delivery, and can be manufactured to look and feel almost like existing needle sets yet still incorporate the skin contact sensing mechanism 10 within the needle 20 and tubing 16 set. This sensing mechanism 10 comprises an activation mechanism 25 in the form of a contact member or projecting spring-arm 18 or that is located toward the bottom of housing 12. The spring-arm 18 size can be adjusted before manufacture to create a device that can precisely determine an exact height for which the needle body 20 has lifted off the surface 50 of the skin during needle dislodgement. For purposes of this disclosure, the term "dislodgement" shall mean a condition where the needle tip has exited the skin, or the housing has lifted off a certain distance from the skin.

The spring-arm 18 is spring-loaded (e.g. with torsion spring 28 shown in FIG. 3A and FIG. 4), and only remains in close apposition to the bottom of the needle body 20 if the tape 52 used to secure the needle 20 it can hold the needle 20 flat down against the skin 50 (see FIG. 1A). The tape 52 can secure the housing 12 and flaps 14, holding the housing 12 and flaps 14 against the skin 50 and/or spring arm 18 (see FIG. 1A'). Housing 12 may also include a cover 32h, needle guide 44, tubing port 42, and flaps 14.

Referring to the dislodged/released orientation shown in FIG. 1 B, when the needle 20 lifts from the body 50, as occurs during most needle dislodgements, the spring-arm 18 swings open.

Figure 2A:
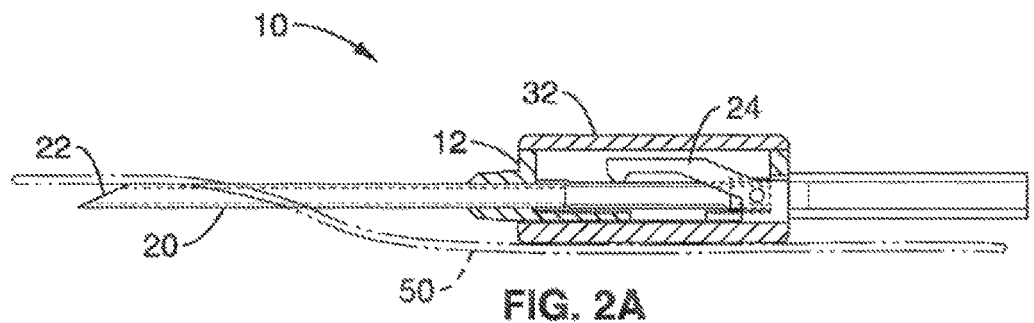
FIG. 2A is a cross-sectional view of the sensing mechanism of FIG. 1A.
Figure 2B:
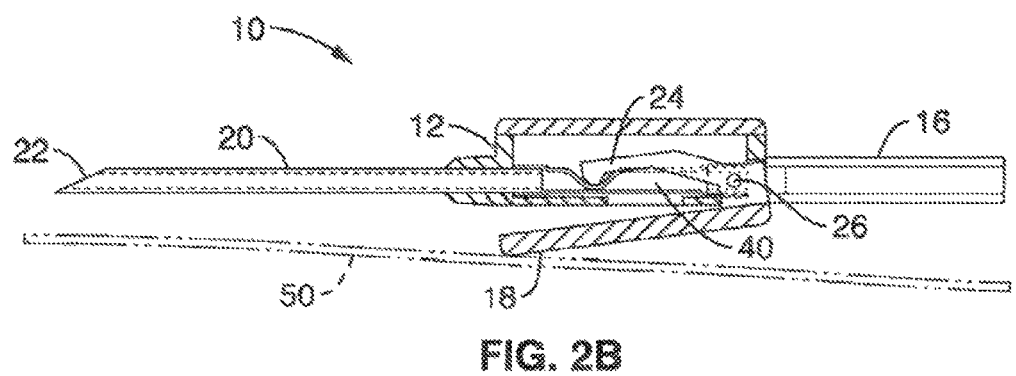
FIG. 2B is a cross-sectional view of the sensing mechanism of FIG. 1A in a released orientation.

As seen in the sectional views of FIG. 2A and FIG. 2B, the spring-arm 18 is coupled mechanically within the interior of housing 12 to a flow termination mechanism comprising a compression lever 24 that forms a pinch valve with tube 40 to stop or significantly limit fluid flow via mechanical disruption of the flow path, e.g. compression or pinching of a soft section 40 of tubing within the needle 20 and flow path. A torsion spring 28 translates movement of the spring-arm 18 into movement of the compression lever 18 via hinge 46 and pins 26 that are disposed in the housing 12 (see FIG. 4).

Figure 3A:
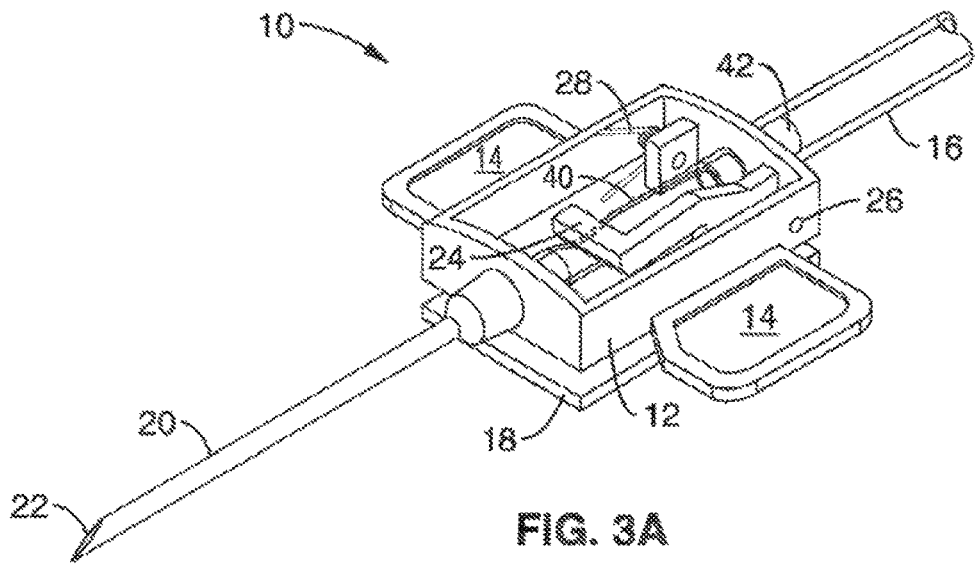
FIG. 3A is a perspective view of the sensing mechanism of FIG. 1A with the top cover removed.
Figure 3B:
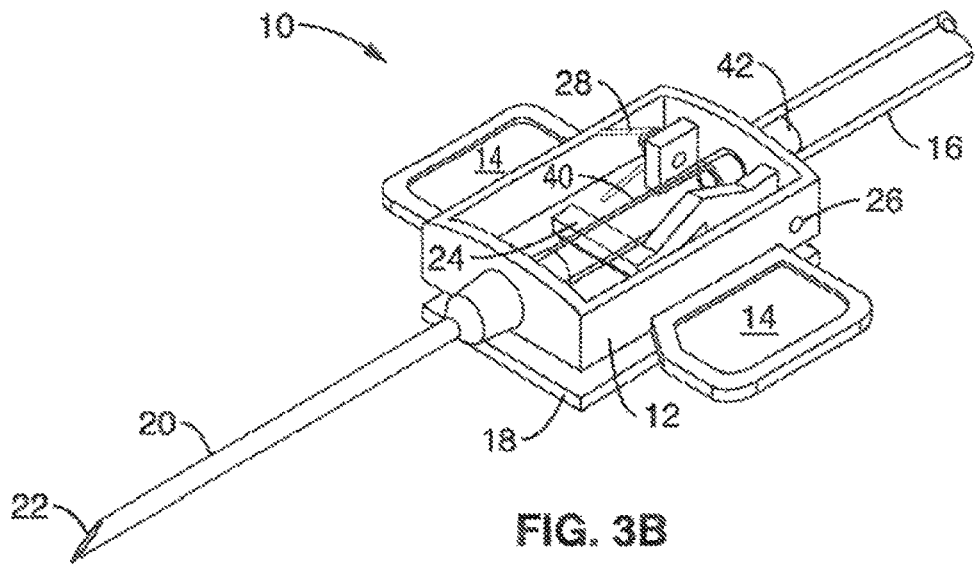
FIG. 3B is a perspective view of an alternative sensing mechanism of FIG. 1 A with integrated tube and housing.
Figure 4:
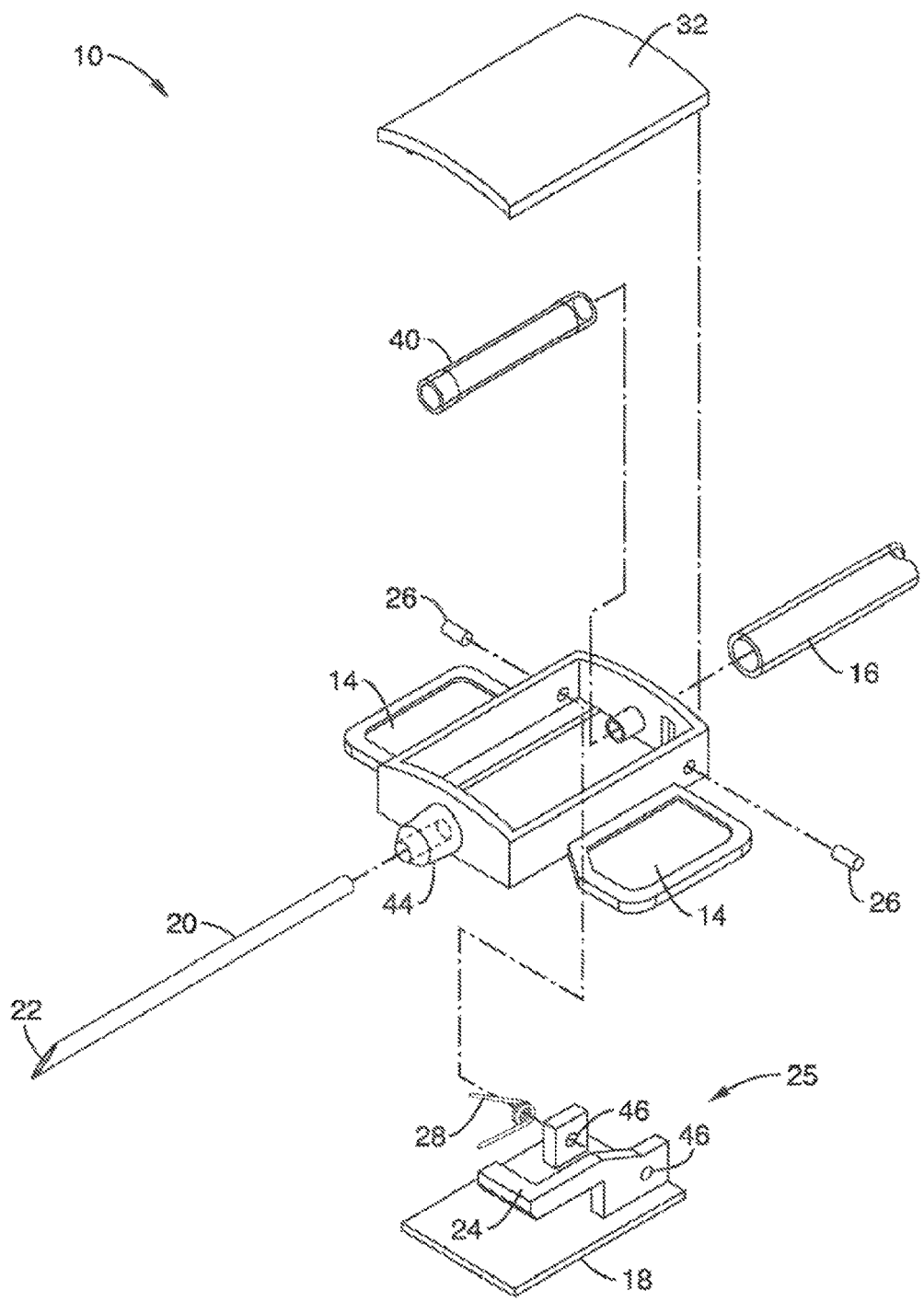
FIG. 4 is an exploded perspective view of the sensing mechanism of FIG. 1A.

The embodiment shown in FIG. 3A and FIG. 4 shows compressible tube 40 as a separate structure that is installed into the housing 12. However, it is contemplated that the housing 12 and tube 40 may be formed from one integral, contiguous piece, by forming a tube 40 from the housing 12 using a thin-wall tube 40, thus making it compliant. Ideally, the compression lever 24 would be disposed underneath tube 40 and rotate upward to form a pinch valve, as shown in FIG. 3B. A two-stage molding process using soft materials for integrated tube section 40 may also be used.

When tape 52 holds the needle down in the lodged configuration of FIG. 1A and FIG. 2A, the spring arm 18 is pushed closed against the housing 12, thus keeping the compression lever 24 off of tubing 40. For purposes of clarity, the tape 52 is shown disposed over needle 20 in FIG. 1 A. However, it is appreciated that tape 52 will often be disclosed over the housing 12 and tabs 14.

When the tape 52 falls off, and the needle tip 22 is dislodged (configuration of FIG. 1B and FIG. 2B), the needle 20 lifts up, allowing the swing arm 18 to open under the pressure of the torsion spring 28, thus forcing the compression lever 24 downward, pinching tubing 40 and stopping flow to the needle 20.

When tape 52 holds the housing 12 down in the lodged configuration of FIG. 1A' and FIG. 2A', the spring arm 18 is pushed closed against the housing 12, thus keeping the compression lever 24 off of tubing 40. For purposes of clarity, the tape 52 is shown disposed over housing 12 in FIG. 1A'.

Figure 1B:
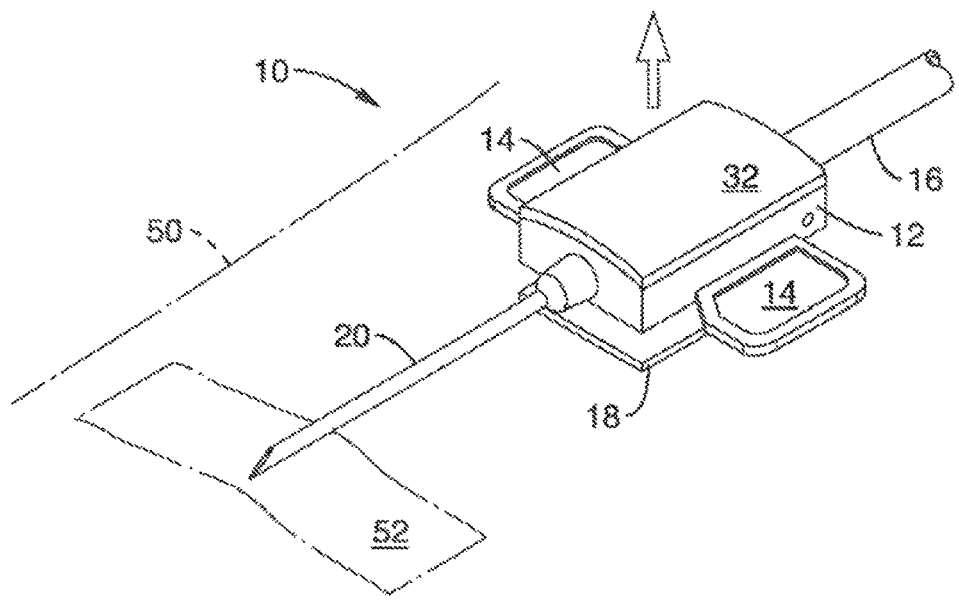
FIG. 1B is a perspective view of the sensing mechanism of FIG. 1A in a released orientation.
Figure 1A:
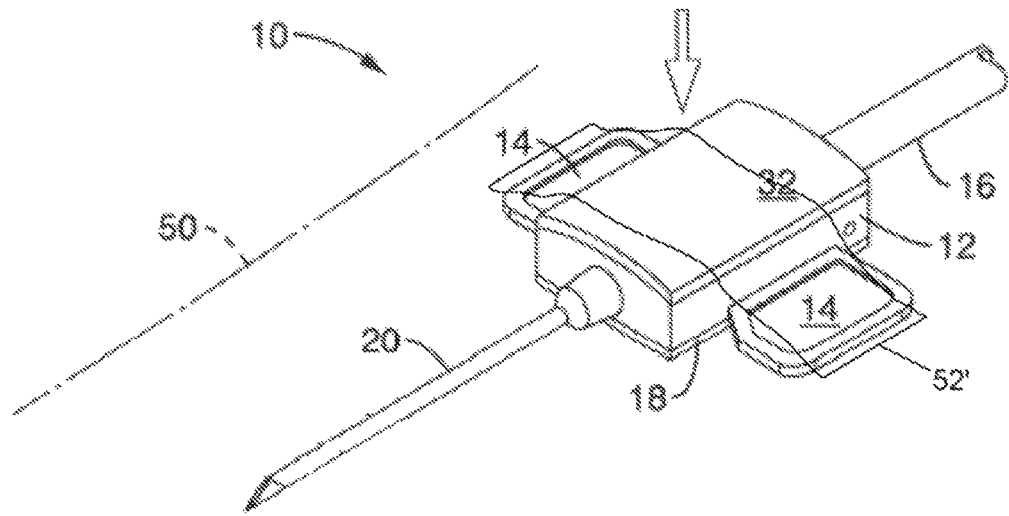
Figure 1B:
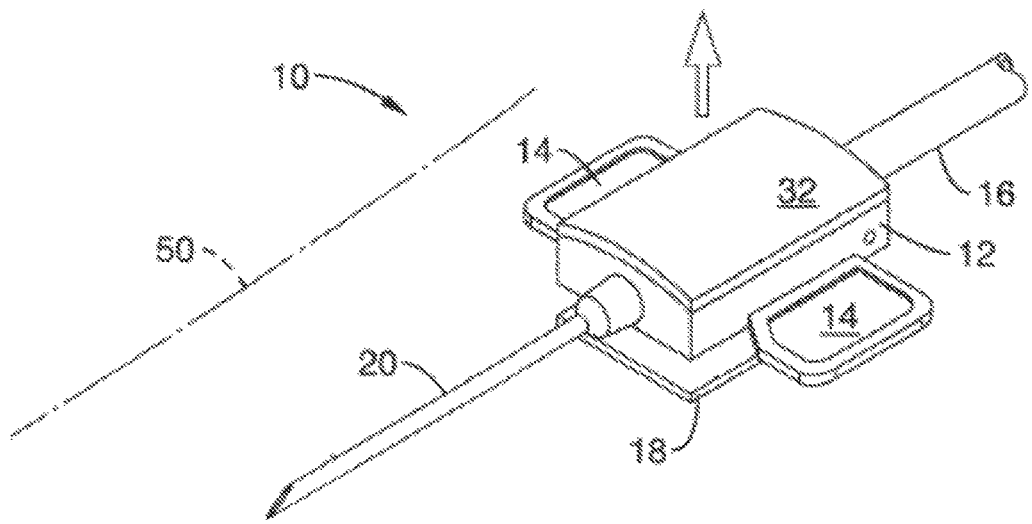

When the tape 52 falls off or is removed from the housing 12 and tabs 14 (or the needle tip 22, as shown in FIGS. 1A and 1B), and the needle tip 22 is dislodged (configuration of FIG. 1B' and FIG. 2B), the housing 12 lifts up, allowing the swing arm 18 to open under the pressure of the torsion spring 28, thus forcing the compression lever 24 downward, pinching tubing 40 and stopping flow to the needle 20.

The integrated design of the compression lever 24 and the spring-arm 18 work synergistically in both detecting problematic dislodgement and immediately solving it. Importantly, system 10 is configured to continuously occlude the tubing at all times during dislodgement. This stops flow and importantly, raises back pressure high enough that a machine pumping the alarm will be triggered to automatically stop pumping.

Figure 5A:
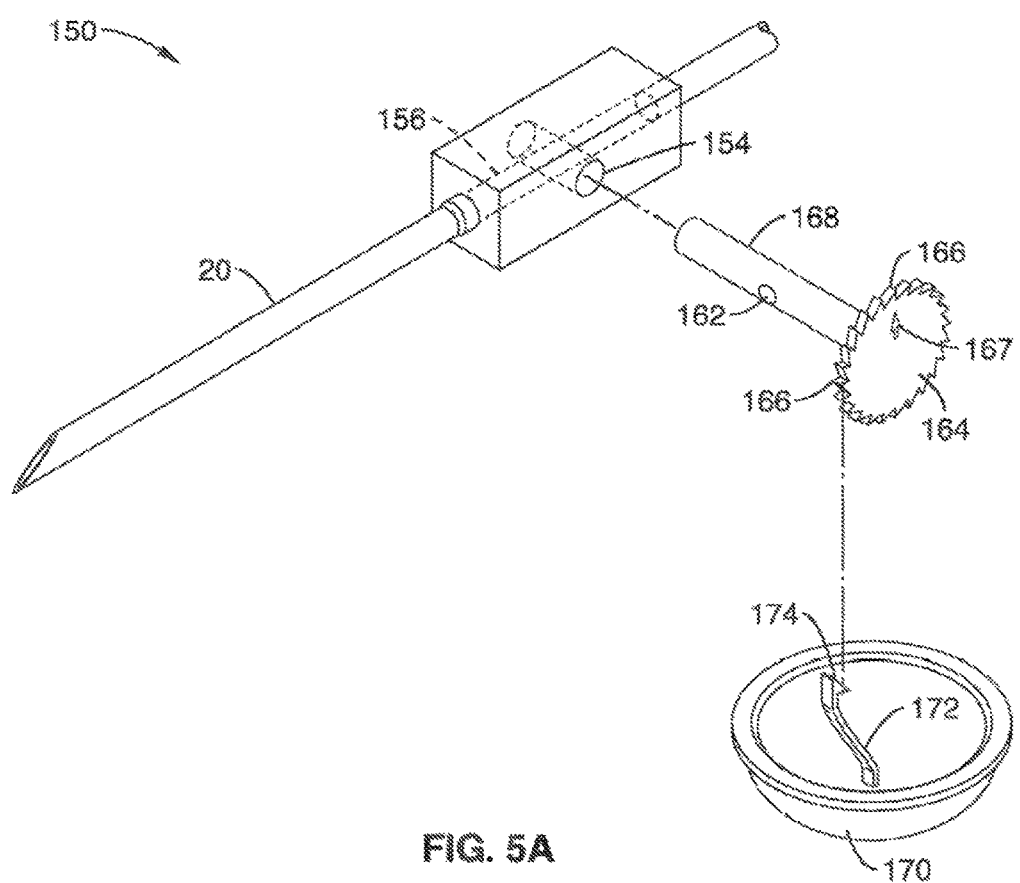
FIG. 5A shows a perspective view of a rotary-valve sensing mechanism in accordance with the present disclosure.
Figure 5B:
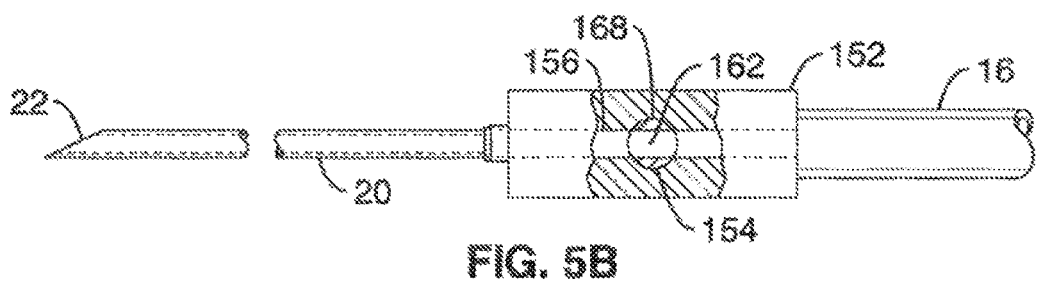
FIG. 5B shows a cutout side view of the rotary-valve sensing mechanism of FIG. 5A in an open configuration.
Figure 5C:
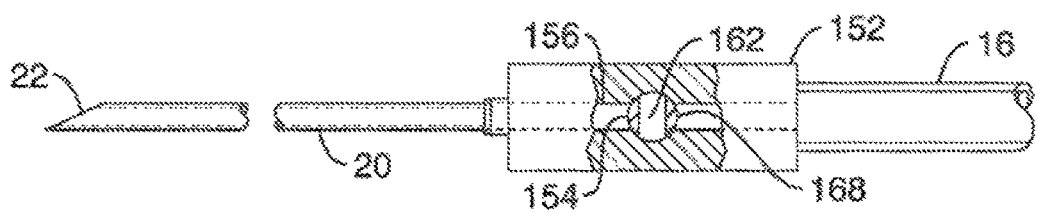
FIG. 5C shows a cutout side view of the rotary-valve sensing mechanism of FIG. 5A in a closed configuration.

FIG. 5A through FIG. 5C show an embodiment incorporating a rotary-valve sensing mechanism/system 150, which includes a housing 152 for receiving tube 16 and needle 20. Housing 152 further includes a central channel 156 in communication with needle 20 and tube 16 for allowing delivery of fluid there between. An aperture 154 runs through channel 156 in approximately an orthogonal orientation, with the aperture 154 configured to receive rod 168 to form a rotary valve, that is coupled to ratchet wheel 164. Rod 168 comprises a through hole 162 that has a diameter approximately the size of channel 156, and is located on rod 168 to line up with channel 156 when in an open configuration, as shown in the side view of FIG. 5B. A sealing mechanism, such as o-ring 312 shown in FIG. 7C, may also be disposed on rod 168 to seal the rotary valve aperture 154.

One end of rod 168 comprises a ratchet wheel 164, which along with contact member/button 170 form an activation mechanism to open and close the rotary valve rod 168. Contact member 170 comprises a compliant, dome-shaped diaphragm that contacts the patient's skin and acts as a return spring that is loaded when pressing inward on the patient. The spring-loaded actuation mechanism of button 170 is further detailed with reference to button 210 shown in FIG. 6A through 6C, which operates in a similar, if not identical, manner. Button 170 comprises an elongate catch 172 that emanates from the bottom of the inside wall of the button. Catch 172 has a hooked distal end 174 that is configured to interface with teeth 166 of ratchet wheel 164 of rod 168 to form a rotary valve-based flow termination mechanism.

When in the compressed state, the catch 162 of button 170 is in an extended linear position toward housing 152 and above ratchet wheel 164. This forms the open state of the rotary valve as seen in the cut-out side view of FIG. 5B (ratchet wheel 164 and button 170 removed for clarity), with through hole 162 lined up to be substantially concentric with the central channel 156 of the housing. Fluid flow is thus allowed between the tube 16 and the needle 22.

When needle 20 is dislodged from the patient's skin, button 170 expands downward from the housing body 152 to its biased, uncompressed state, which causes the catch 172 to move downward such that distal end 174 catches teeth 166 of ratchet wheel 174 to rotate rod 162 (e.g. 90°) within aperture 154. This results in the through hole 162 no longer being in alignment with central channel 156, thus terminating or restricting flow through channel 156 from tube 16 to needle 20 as seen in the cut-out side view of FIG. 5C (ratchet wheel 164 and button 170 removed for clarity). To reset the flow to open upon re-insertion of the needle 20 and compression of the button 170, the ratchet wheel 164 may simply be rotated e.g. 90° clockwise to the original position, such that indicia 167 lines up in the proper position. The rotary valve mechanism 150 thus converts the linear motion of button 170 to a rotational motion.

Figure 6A:
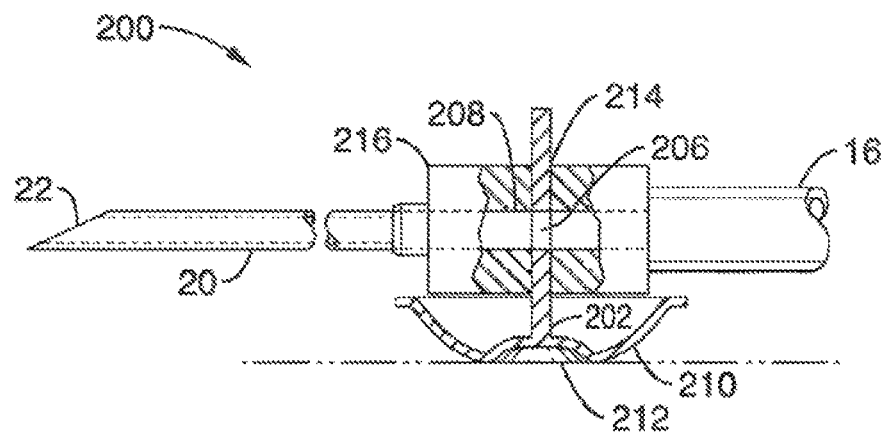
FIG. 6A through FIG. 6C show sectional side views of a slider valve-based sensing system in accordance with the present disclosure.
Figure 6B:
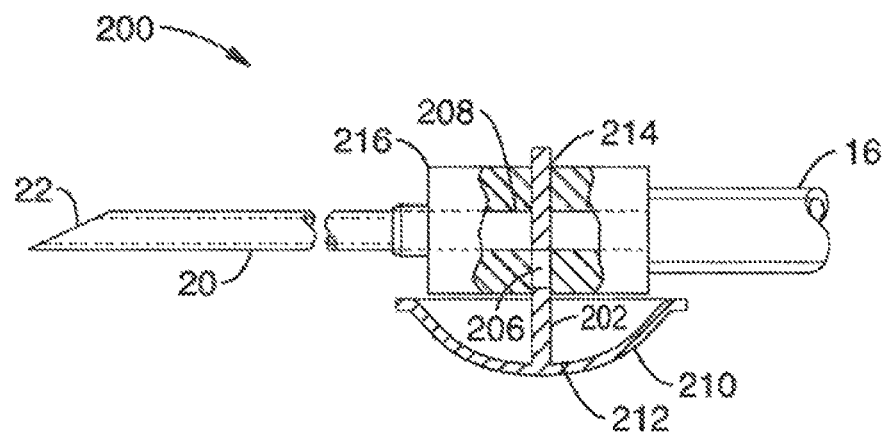
Figure 6C:
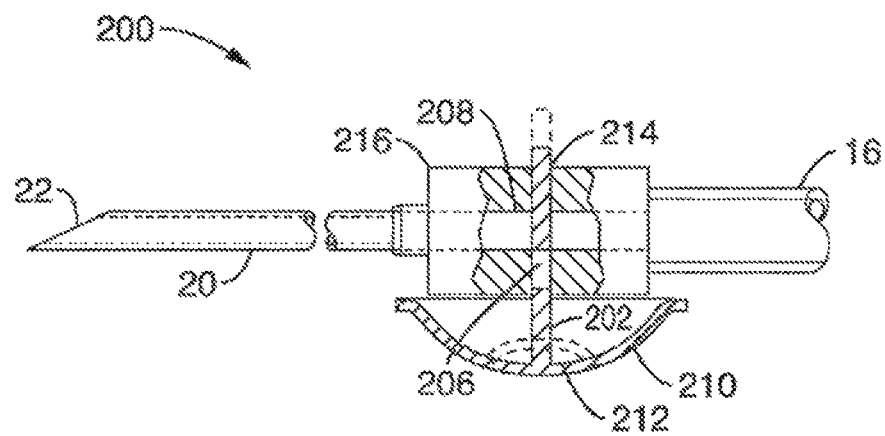

FIG. 6A through FIG. 6C show sectional side views of a slider valve, or shuttle valve-based sensing system 200 in accordance with the present disclosure. FIG. 6A shows the system 200 in an open configuration, allowing fluid flow between needle 20 and tube 16. Housing 216 includes a central channel 208 in communication with needle 20 and tube 16. An aperture 214 runs through channel 208 in approximately an orthogonal orientation, with the aperture 214 configured to receive slider pin 202. Slider pin 202 comprises a through hole 206 that has a diameter approximately the size of channel 208, and is located to line up with channel 208 in the open configuration of FIG. 6A. In this configuration, contact member or button 210, which is coupled to one end of the slider pin 202, is compressed against the patient's skin 212. Button 210 comprises a compliant, dome-shaped wall that acts as a return spring that is loaded when pressing inward on the patient. Slider pin 202 may be molded with button 210 as one contiguous piece of material (e.g. silicone), or may be attached to the button 210 via adhesive or other attachment means.

As seen in FIG. 6B, which shows the system 200 in a closed configuration, and FIG. 6C, which shows the system 200 in an open (dashed line) configuration, the slider pin 202 is configured to reciprocate within aperture 214 of the housing 216. When needle 20 is dislodged from the patient's skin 212, button 210 expands, which causes the slider pin 202 to retract out of aperture 214. This results in the through-hole 206 no longer being in alignment with central channel 208, thus terminating or restricting flow through channel 208 from tube 16 to needle 20 to form a shuttle valve/flow termination mechanism.

Figure 7A:
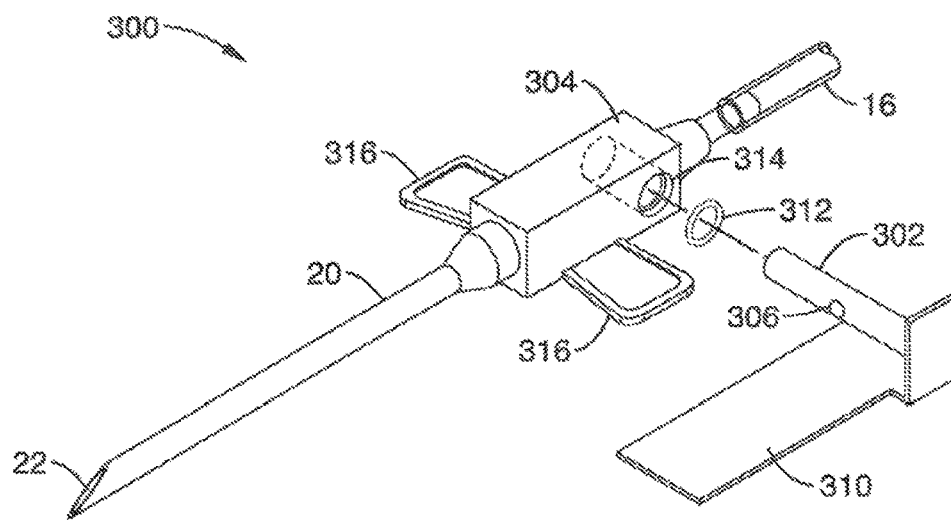
FIG. 7A shows an exploded perspective view of a preferred embodiment incorporating a rotary valve mechanism in accordance with the present disclosure.

FIG. 7A shows an exploded perspective view of a preferred embodiment incorporating a rotary valve-sensing mechanism/system 300, which includes a housing 304 for receiving tube 16 and needle 20. Housing 304 further includes tabs 316 and a central channel 308 (FIG. 7B) in communication with needle 20 and tube 16 for allowing delivery of fluid there between. An aperture 314 runs through channel 308 in approximately an orthogonal orientation, with the aperture 314 configured to receive rod 302 that is coupled to spring-arm/lever 310. Rod 302 comprises a through hole 306 that has a diameter approximately the size of channel 308, and is located on rod 302 to line up with channel 308 when in an open configuration, i.e. rod 302 and spring-arm 310.

Figure 7B:
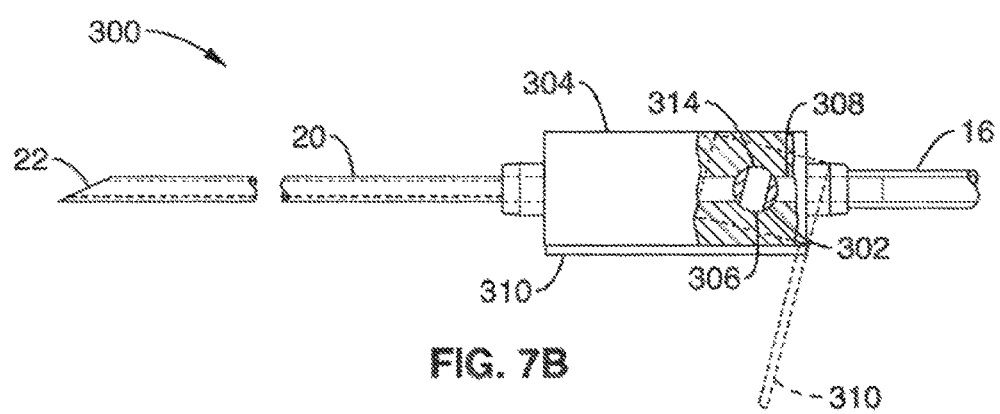
FIG. 7B is a side view of the rotary valve mechanism of FIG. 7A in a closed configuration.

As seen in FIG. 7B, which shows the contact member or spring-arm 310 of system 300 in a closed configuration (dashed line open away from housing 304) and open configuration (solid line against the housing 304), the rod 302 is configured to rotate within aperture 314 of the housing 304. When needle 20 is dislodged from the patient's skin, lever 310 retracts outward from the housing body (e.g. from a biasing member (not shown) such as a torsion spring or the like), which causes the rod 302 to rotate within aperture 214. The activation mechanism of spring-arm 310 thus results in the through hole 306 no longer being in alignment with central channel 308, thus terminating or restricting flow through channel 308 from tube 16 to needle 20, i.e. forming a flow termination mechanism.

Figure 7C:
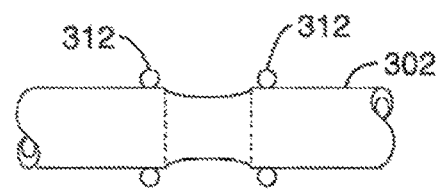
FIG. 7C is a side view of the sealing mechanism of FIG. 7A.

As shown in FIG. 7C, the rod 302 may comprise a pair of o-rings 312 that are disposed on the rod 302 at the periphery of the openings of aperture 304 to seal aperture 304 from possible leakage of fluids within the central channel 308.

From the description herein, it will be appreciated that that the present disclosure encompasses multiple embodiments which include, but are not limited to, the following:

1. An apparatus for automatic termination of flow for fluid delivery, the apparatus comprising: a housing configured for coupling a fluid delivery tube to a needle configured for subcutaneous delivery of fluid within a tissue of a patient; a spring-loaded activation mechanism coupled to the housing; wherein the activation mechanism comprises a first orientation corresponding to a condition where the housing is disposed substantially adjacent to the tissue and the needle lodged within the tissue; wherein the activation mechanism comprises a second orientation corresponding to a condition where the housing is disposed away from the tissue or the needle is dislodged from the tissue; a flow termination mechanism coupled to the activation mechanism; wherein the flow termination mechanism comprises an open configuration allowing flow from the fluid delivery tube to the needle when the activation mechanism is in the first orientation; and wherein the flow termination mechanism comprises a closed configuration substantially terminating flow from the fluid delivery tube to the needle when the activation mechanism is in the second orientation.

2. The apparatus of any preceding embodiment: wherein the activation mechanism comprises a contact member configured to be disposed adjacent the patient's skin when the activation mechanism is in the first orientation; and wherein the contact member articulates with respect to the housing to the second orientation.

3. The apparatus of any preceding embodiment: wherein the flow termination mechanism comprises a pinch valve that substantially terminates flow from the fluid delivery tube to the needle when the activation mechanism is in the second orientation.

4. The apparatus of any preceding embodiment: wherein the contact member and flow termination mechanism comprise a spring-arm and compression lever to form a pinch valve; wherein the spring-arm is disposed adjacent the housing when positioned in the first orientation; wherein the spring-arm articulates away from the housing in the second orientation; and wherein the compression lever articulates in response to articulation of the swing arm in the second orientation to pinch-off flow from the fluid delivery tube to the needle when the activation mechanism is in the second orientation.

5. The apparatus of any preceding embodiment: wherein the housing comprises a compliant tube coupling the fluid delivery tube to the needle; and wherein the compression lever articulates against the compliant tube in the second orientation to terminate flow from the fluid delivery tube to the needle.

6. The apparatus of any preceding embodiment: wherein the contact member comprises a dome-shaped button that is biased in an expanded configuration corresponding to the second orientation; and wherein the button is loaded in a compressed configuration adjacent the patient's skin in the first orientation.

7. The apparatus of any preceding embodiment: wherein the flow termination mechanism comprises a shuttle valve coupled to the contact member; and wherein the contact member affects translation of the shuttle valve from within the housing from the first orientation to the second orientation.

8. The apparatus of any preceding embodiment: wherein the contact member comprises a dome-shaped button that is biased in an expanded configuration corresponding to the second orientation; and wherein the button is loaded in a compressed configuration adjacent the patient's skin in the first orientation.

9. The apparatus of any preceding embodiment: wherein the flow termination mechanism comprises a rotary valve coupled the contact member; and wherein the contact member affects rotation of the rotary valve from within the housing from the first orientation to the second orientation.

10. The apparatus of any preceding embodiment: wherein the contact member and rotary valve comprise a lever and a rod, the rod being disposed in an aperture within the housing; the housing comprising a central channel allowing fluid flow from the fluid delivery tube to the needle; wherein the rod comprises a through-hole that is in alignment with the central channel when in the first orientation; wherein the spring-arm is disposed adjacent the housing when positioned in the first orientation and articulates away from the housing in the second orientation; and wherein the rod rotates in response to articulation of the swing arm in the second orientation to rotate the through-hole out of alignment with the central channel to inhibit fluid flow from the fluid delivery tube to the needle when the activation mechanism is in the second orientation.

11. The apparatus of any preceding embodiment: wherein the contact member and rotary valve comprise a button and a rod, the rod being disposed in an aperture within the housing; the housing comprising a central channel allowing fluid flow from the fluid delivery tube to the needle; wherein the rod comprises a through-hole that is in alignment with the central channel when in the first orientation; wherein the button is adjacent the housing when positioned in the first orientation and retracts away from the housing in the second orientation; and wherein the rod rotates in response to retraction of the button in the second orientation to rotate the through-hole out of alignment with the central channel to inhibit fluid flow from the fluid delivery tube to the needle when the activation mechanism is in the second orientation.

12. A system for automatic termination of flow for a fluid delivery, the system comprising: a fluid delivery tube and a needle configured for subcutaneous delivery of fluid within a tissue of a patient; a housing configured for coupling the fluid delivery tube to the needle; a spring-loaded activation mechanism coupled to the housing; wherein the activation mechanism comprises a first orientation corresponding to a condition where the housing is disposed substantially adjacent to the tissue and the needle lodged within the tissue; wherein the activation mechanism comprises a second orientation corresponding to a condition where the housing is disposed away from the tissue or the needle being dislodged from the tissue; a flow termination mechanism coupled to the activation mechanism; wherein the flow termination mechanism comprises an open configuration allowing flow from the fluid delivery tube to the needle when the activation mechanism is in the first orientation; and wherein the flow termination mechanism comprises a closed configuration substantially terminating flow from the fluid delivery tube to the needle when the activation mechanism is in the second orientation.

13. The system of any preceding embodiment: wherein the activation mechanism comprises a contact member configured to be disposed adjacent the patient's skin when the activation mechanism is in the first orientation; and wherein the contact member articulates with respect to the housing to the second orientation.

14. The system of any preceding embodiment: wherein the flow termination mechanism comprises a pinch valve that substantially terminates flow from the fluid delivery tube to the needle when the activation mechanism is in the second orientation.

15. The system of any preceding embodiment: wherein the contact member and flow termination mechanism comprise a spring-arm and compression lever to form a pinch valve; wherein the spring-arm is disposed adjacent the housing when positioned in the first orientation; wherein the spring-arm articulates away from the housing in the second orientation; and wherein the compression lever articulates in response to articulation of the swing arm in the second orientation to pinch-off flow from the fluid delivery tube to the needle when the activation mechanism is in the second orientation.

16. The system of any preceding embodiment: wherein the housing comprises a compliant tube coupling the fluid delivery tube to the needle; and wherein the compression lever articulates against the compliant tube in the second orientation to terminate flow from the fluid delivery tube to the needle.

17. The system of any preceding embodiment: wherein the contact member comprises dome-shaped button that is biased in an expanded configuration corresponding to the second orientation; and wherein the button is loaded in a compressed configuration adjacent the patient's skin in the first orientation.

18. The system of any preceding embodiment: wherein the flow termination mechanism comprises a shuttle valve coupled to the contact member; and wherein the contact member affects translation of the shuttle valve from within the housing from the first orientation to the second orientation.

19. The system of any preceding embodiment: wherein the contact member comprises a spring-loaded, dome-shaped button that is biased in an expanded configuration corresponding to the second orientation; and wherein the button is loaded in a compressed configuration adjacent the patient's skin in the first orientation.

20. The system of any preceding embodiment: wherein the flow termination mechanism comprises a rotary valve coupled to the contact member; and wherein the contact member affects rotation of the rotary valve from within the housing from the first orientation to the second orientation.

21. The system of any preceding embodiment: wherein the contact member and rotary valve comprise a lever and a rod, the rod being disposed in an aperture within the housing; the housing comprising a central channel allowing fluid flow from the fluid delivery tube to the needle; wherein the rod comprises a through-hole that is in alignment with the central channel when in the first orientation; wherein the spring-arm is disposed adjacent the housing when positioned in the first orientation and articulates away from the housing in the second orientation; and wherein the rod rotates in response to articulation of the swing arm in the second orientation to rotate the through-hole out of alignment with the central channel to inhibit fluid flow from the fluid delivery tube to the needle when the activation mechanism is in the second orientation.

22. The system of any preceding embodiment: wherein the contact member and rotary valve comprise a button and a rod, the rod being disposed in an aperture within the housing; the housing comprising a central channel allowing fluid flow from the fluid delivery tube to the needle; wherein the rod comprises a through-hole that is in alignment with the central channel when in the first orientation; wherein the button is adjacent the housing when positioned in the first orientation and retracts away from the housing in the second orientation; and wherein the rod rotates in response to retraction of the button in the second orientation to rotate the through-hole out of alignment with the central channel to inhibit fluid flow from the fluid delivery tube to the needle when the activation mechanism is in the second orientation.

23. A method for automatic termination of flow for fluid delivery within a patient, the method comprising: coupling a housing to a surface of a patient's tissue; the housing configured for coupling a fluid delivery tube to a needle for delivery of fluid within the tissue of a patient; preloading a spring-loaded activation mechanism at a first orientation corresponding to a condition where the housing is disposed adjacent to the tissue and the needle lodged within the tissue; wherein a flow termination mechanism coupled to the activation mechanism is disposed in an open configuration allowing flow from the fluid delivery tube to the needle when the activation mechanism is in the first orientation; upon release of the housing away from the tissue or the needle being dislodged from the tissue, advancing the activation mechanism to a second orientation; and switching the flow termination mechanism to a closed configuration to substantially terminate flow from the fluid delivery tube to the needle.

24. The method of any preceding embodiment: wherein the flow termination mechanism comprises a pinch valve; and wherein switching the flow termination mechanism to a closed configuration comprises pinching-off flow between the fluid delivery tube and the needle.

25. The method of any preceding embodiment: wherein the activation mechanism comprises a contact member disposed adjacent the housing when positioned in the first orientation; wherein the contact member articulates away from the housing in the second orientation; wherein the housing comprises a compliant tube coupling the fluid delivery tube to the needle; and wherein flow termination mechanism comprises a compression lever that articulates against the compliant tube in the second orientation to terminate flow from the fluid delivery tube to the needle.

26. The method of any preceding embodiment: wherein the activation mechanism comprises a contact member disposed adjacent the housing when positioned in the first orientation; wherein the contact member articulates away from the housing in the second orientation; wherein the flow termination mechanism comprises a rotary valve coupled to the contact member; and wherein the contact member affects rotation of the rotary valve from within the housing from the first orientation to the second orientation.

27. The method of any preceding embodiment: wherein the contact member and rotary valve comprise a lever and a rod, the rod being disposed in an aperture within the housing; the housing comprising a central channel allowing fluid flow from the fluid delivery tube to the needle; wherein the rod comprises a through-hole that is in alignment with the central channel when in the first orientation; wherein the spring-arm is disposed adjacent the housing when positioned in the first orientation and articulates away from the housing in the second orientation; and wherein the rod rotates in response to articulation of the swing arm in the second orientation to rotate the through-hole out of alignment with the central channel to inhibit fluid flow from the fluid delivery tube to the needle when the activation mechanism is in the second orientation.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

We claim:

1. An apparatus for automatic termination of flow for fluid delivery, the apparatus comprising:
    a housing configured for coupling a fluid delivery tube to a needle configured for subcutaneous delivery of fluid within a tissue of a patient;
    a spring-loaded activation mechanism coupled to the housing;
    wherein the spring-loaded activation mechanism comprises a first orientation corresponding to a condition where the housing is disposed substantially adjacent to the tissue and the needle is lodged within the tissue;
    wherein the spring-loaded activation mechanism comprises a second orientation corresponding to a condition where the housing is disposed away from the tissue or the needle is dislodged from the tissue;
    a flow termination mechanism coupled to the spring-loaded activation mechanism;
    wherein the flow termination mechanism comprises an open configuration allowing flow from the fluid delivery tube to the needle when the spring-loaded activation mechanism is in the first orientation;
    wherein the flow termination mechanism comprises a closed configuration substantially terminating flow from the fluid delivery tube to the needle when the spring-loaded activation mechanism is in the second orientation;

wherein the spring-loaded activation mechanism comprises a contact member configured to be disposed adjacent the patient's skin when the spring-loaded activation mechanism is in the first orientation;

wherein the contact member articulates with respect to the housing to the second orientation; and wherein the flow termination mechanism comprises a pinch valve that substantially terminates flow from the fluid delivery tube to the needle when the spring-loaded activation mechanism is in the second orientation.

2. The apparatus of claim 1:
wherein the contact member and flow termination mechanism comprise a spring-arm and a compression lever.

3. The apparatus of claim 2:
wherein the spring-arm is disposed adjacent the housing when positioned in the first orientation.

4. The apparatus of claim 3:
wherein the spring-arm articulates away from the housing in the second orientation.

5. The apparatus of claim 4:
wherein the compression lever articulates in response to articulation of the spring-arm in the second orientation to pinch-off flow from the fluid delivery tube to the needle when the spring-loaded activation mechanism is in the second orientation.

6. The apparatus of claim 1:
wherein the housing comprises a compliant tube coupling the fluid delivery tube to the needle.

7. An apparatus for automatic termination of flow for fluid delivery, the apparatus comprising:
a housing configured for coupling a fluid delivery tube to a needle configured for subcutaneous delivery of fluid within a tissue of a patient;
a spring-loaded activation mechanism coupled to the housing;
wherein the spring-loaded activation mechanism comprises a first orientation corresponding to a condition where the housing is disposed substantially adjacent to the tissue and the needle is lodged within the tissue;
wherein the spring-loaded activation mechanism comprises a second orientation corresponding to a condition where the housing is disposed away from the tissue or the needle is dislodged from the tissue;
a flow termination mechanism coupled to the spring-loaded activation mechanism;
wherein the flow termination mechanism comprises an open configuration allowing flow from the fluid delivery tube to the needle when the spring-loaded activation mechanism is in the first orientation;
wherein the flow termination mechanism comprises a closed configuration substantially terminating flow from the fluid delivery tube to the needle when the spring-loaded activation mechanism is in the second orientation;
wherein the spring-loaded activation mechanism comprises a contact member configured to be disposed adjacent the patient's skin when the spring-loaded activation mechanism is in the first orientation;
wherein the contact member articulates with respect to the housing to the second orientation;
wherein the contact member and flow termination mechanism comprise a spring-arm and a compression lever to form a pinch valve;

wherein the spring-arm is disposed adjacent the housing when positioned in the first orientation;
wherein the spring-arm articulates away from the housing in the second orientation; and
wherein the compression lever articulates in response to articulation of the spring-arm in the second orientation to pinch-off flow from the fluid delivery tube to the needle when the spring-loaded activation mechanism is in the second orientation.

8. The apparatus of claim 7:
wherein the housing comprises a compliant tube coupling the fluid delivery tube to the needle; and
wherein the compression lever articulates against the compliant tube in the second orientation to terminate flow from the fluid delivery tube to the needle.

9. An apparatus for automatic termination of flow for fluid delivery, the apparatus comprising:
a housing configured for coupling a fluid delivery tube to a needle configured for subcutaneous delivery of fluid within a tissue of a patient;
a spring-loaded activation mechanism coupled to the housing;
wherein the spring-loaded activation mechanism comprises a first orientation corresponding to a condition where the housing is disposed substantially adjacent to the tissue and the needle is lodged within the tissue;
wherein the spring-loaded activation mechanism comprises a second orientation corresponding to a condition where the housing is disposed away from the tissue or the needle is dislodged from the tissue;
a flow termination mechanism coupled to the spring-loaded activation mechanism;
wherein the flow termination mechanism comprises an open configuration allowing flow from the fluid delivery tube to the needle when the spring-loaded activation mechanism is in the first orientation;
wherein the flow termination mechanism comprises a closed configuration substantially terminating flow from the fluid delivery tube to the needle when the spring-loaded activation mechanism is in the second orientation;
wherein the spring-loaded activation mechanism comprises a contact member configured to be disposed adjacent the patient's skin when the spring-loaded activation mechanism is in the first orientation;
wherein the contact member articulates with respect to the housing to the second orientation;
wherein the contact member comprises a dome-shaped diaphragm that is biased in an expanded configuration corresponding to the second orientation; and wherein the dome-shaped diaphragm is loaded in a compressed configuration adjacent the patient's skin in the first orientation.

10. A system for automatic termination of flow for a fluid delivery, the system comprising:
a fluid delivery tube and a needle configured for subcutaneous delivery of fluid within a tissue of a patient;
a housing configured for coupling the fluid delivery tube to the needle; a spring-loaded activation mechanism coupled to the housing;
wherein the spring-loaded activation mechanism comprises a first orientation corresponding to a condition where the housing is disposed substantially adjacent to the tissue and the needle is lodged within the tissue;
wherein the spring-loaded activation mechanism comprises a second orientation corresponding to a condition where the housing is disposed away from the tissue or the needle being dislodged from the tissue;
a flow termination mechanism coupled to the spring-loaded activation mechanism;
wherein the flow termination mechanism comprises an open configuration allowing flow from the fluid delivery tube to the needle when the spring-loaded activation mechanism is in the first orientation;
wherein the flow termination mechanism comprises a closed configuration substantially terminating flow from the fluid delivery tube to the needle when the spring-loaded activation mechanism is in the second orientation;
wherein the spring-loaded activation mechanism comprises a contact member configured to be disposed adjacent the patient's skin when the spring-loaded activation mechanism is in the first orientation;
wherein the contact member articulates with respect to the housing to the second orientation; and
wherein the flow termination mechanism comprises a pinch valve that substantially terminates flow from the fluid delivery tube to the needle when the spring-loaded activation mechanism is in the second orientation.

11. The apparatus of claim 10:
wherein the contact member and flow termination mechanism comprise a spring-arm and a compression lever.

12. The apparatus of claim 11:
wherein the spring-arm is disposed adjacent the housing when positioned in the first orientation.

13. The apparatus of claim 12:
wherein the spring-arm articulates away from the housing in the second orientation.

14. The apparatus of claim 13:
wherein the compression lever articulates in response to articulation of the spring-arm in the second orientation to pinch-off flow from the fluid delivery tube to the needle when the spring-loaded activation mechanism is in the second orientation.

15. A system of for automatic termination of flow for a fluid delivery, the system comprising:
a fluid delivery tube and a needle configured for subcutaneous delivery of fluid within a tissue of a patient;
a housing configured for coupling the fluid delivery tube to the needle; a spring-loaded activation mechanism coupled to the housing;
wherein the spring-loaded activation mechanism comprises a first orientation corresponding to a condition where the housing is disposed substantially adjacent to the tissue and the needle is lodged within the tissue;
wherein the spring-loaded activation mechanism comprises a second orientation corresponding to a condition where the housing is disposed away from the tissue or the needle being dislodged from the tissue;
a flow termination mechanism coupled to the spring-loaded activation mechanism;
wherein the flow termination mechanism comprises an open configuration allowing flow from the fluid delivery tube to the needle when the spring-loaded activation mechanism is in the first orientation;
wherein the flow termination mechanism comprises a closed configuration substantially terminating flow from the fluid delivery tube to the needle when the spring-loaded activation mechanism is in the second orientation;
wherein the spring-loaded activation mechanism comprises a contact member configured to be disposed adjacent the patient's skin when the spring-loaded activation mechanism is in the first orientation;
wherein the contact member articulates with respect to the housing to the second orientation;
wherein the contact member and flow termination mechanism comprise a spring-arm and a compression lever to form a pinch valve;
wherein the spring-arm is disposed adjacent the housing when positioned in the first orientation;
wherein the spring-arm articulates away from the housing in the second orientation; and
wherein the compression lever articulates in response to articulation of the spring-arm in the second orientation to pinch-off flow from the fluid delivery tube to the needle when the spring-loaded activation mechanism is in the second orientation.

16. The system of claim 15:
wherein the housing comprises a compliant tube coupling the fluid delivery tube to the needle; and
wherein the compression lever articulates against the compliant tube in the second orientation to terminate flow from the fluid delivery tube to the needle.

17. A system of for automatic termination of flow for a fluid delivery, the system comprising;
a fluid delivery tube and a needle configured for subcutaneous delivery of fluid within a tissue of a patient;
a housing configured for coupling the fluid delivery tube to the needle; a spring-loaded activation mechanism coupled to the housing;
wherein the spring-loaded activation mechanism comprises a first orientation corresponding to a condition where the housing is disposed substantially adjacent to the tissue and the needle is lodged within the tissue;
wherein the spring-loaded activation mechanism comprises a second orientation corresponding to a condition where the housing is disposed away from the tissue or the needle being dislodged from the tissue;
a flow termination mechanism coupled to the spring-loaded activation mechanism;
wherein the flow termination mechanism comprises an open configuration allowing flow from the fluid delivery tube to the needle when the spring-loaded activation mechanism is in the first orientation;
wherein the flow termination mechanism comprises a closed configuration substantially terminating flow from the fluid delivery tube to the needle when the spring-loaded activation mechanism is in the second orientation;
wherein the spring-loaded activation mechanism comprises a contact member configured to be disposed adjacent the patient's skin when the spring-loaded activation mechanism is in the first orientation;
wherein the contact member articulates with respect to the housing to the second orientation;
wherein the contact member comprises a dome-shaped diaphragm that is biased in an expanded configuration corresponding to the second orientation; and
wherein the dome-shaped diaphragm is loaded in a compressed configuration adjacent the patient's skin in the first orientation.

18. A method for automatic termination of flow for fluid delivery within a patient, the method comprising:
coupling a housing to a surface of a patient's tissue, wherein the housing is configured for coupling a fluid delivery tube to a needle for delivery of fluid within the tissue of a patient;

preloading a spring-loaded activation mechanism at a first orientation corresponding to a condition where the housing is disposed adjacent to the tissue and the needle is lodged within the tissue;

wherein a flow termination mechanism coupled to the spring-loaded activation mechanism is disposed in an open configuration allowing flow from the fluid delivery tube to the needle when the spring-loaded activation mechanism is in the first orientation;

upon release of the housing away from the tissue or the needle being dislodged from the tissue, advancing the spring-loaded activation mechanism to a second orientation; and switching the flow termination mechanism to a closed configuration to substantially terminate flow from the fluid delivery tube to the needle;

wherein the flow termination mechanism comprises a pinch valve; and wherein switching the flow termination mechanism to a closed configuration comprises pinching-off flow between the fluid delivery tube and the needle.

19. The method of claim 18:

wherein the spring-loaded activation mechanism comprises a contact member disposed adjacent the housing when positioned in the first orientation;

wherein the contact member articulates away from the housing in the second orientation;

wherein the housing comprises a compliant tube coupling the fluid delivery tube to the needle; and wherein flow termination mechanism comprises a compression lever that articulates against the compliant tube in the second orientation to terminate flow from the fluid delivery tube to the needle.

20. The apparatus of claim 18:

wherein the housing comprises a compliant tube coupling the fluid delivery tube to the needle; and wherein flow termination mechanism comprises a compression lever that articulates against the compliant tube in the second orientation to terminate flow from the fluid delivery tube to the needle.

* * * * *